United States Patent [19]

Kadefors et al.

[11] Patent Number: 5,318,039
[45] Date of Patent: Jun. 7, 1994

[54] METHOD AND AN APPARATUS IN ELECTROMYOGRAPHY

[75] Inventors: Roland Kadefors; Leif Sandsjö, both of Göteborg; Tommy Öberg, Eksjö, all of Sweden

[73] Assignee: Biolin AB, Mölndal, Sweden

[21] Appl. No.: 973,228

[22] Filed: Nov. 6, 1992

Related U.S. Application Data

[63] Continuation of Ser. No. 558,638, Jul. 27, 1990, abandoned.

[30] Foreign Application Priority Data

Jul. 31, 1989 [SE] Sweden ............................ 8902626-4

[51] Int. Cl.⁵ .......................................... A61B 5/0488
[52] U.S. Cl. ..................................... 128/733; 128/774
[58] Field of Search ............... 128/696, 706, 731, 732, 128/733, 781-782, 774, 905

[56] References Cited

U.S. PATENT DOCUMENTS

| | | | |
|---|---|---|---|
| 4,213,467 | 7/1980 | Stulen et al. | 128/733 |
| 4,579,125 | 4/1986 | Strobl et al. | 128/731 |
| 4,667,513 | 5/1987 | Konno | 73/379 |
| 4,823,804 | 4/1989 | Ghislaine et al. | 128/733 |
| 4,940,058 | 7/1990 | Taff et al. | 128/653 R |
| 4,967,761 | 11/1990 | Nathanielsz | 128/733 |
| 5,086,779 | 2/1992 | DeLuca et al. | 128/733 |

FOREIGN PATENT DOCUMENTS 0306346  8/1989  European Pat. Off. ........ A61B 5/04

*Primary Examiner*—Angela D. Sykes
*Attorney, Agent, or Firm*—Ladas & Parry

[57] ABSTRACT

A method and apparatus for detecting muscular status in which electrodes are connected to the body muscles being investigated for producing analog myoelectric signals which are amplified in an amplifier and fed to an A/D converter connected to a signal processing unit. A signal device is connected to the signal processing unit. The analog signals from the electrodes are converted, after amplification, into binary signals which are frequency-analyzed in the signal processing unit by comparing the appearance and/or position of a frequency spectrum in relation to a predetermined initial position at commencement of the detection. Signals relating to the shift of the frequency spectrum in relation to its initial position are emitted by the signal device or stored in a storage device.

18 Claims, 6 Drawing Sheets

METHOD AND AN APPARATUS IN ELECTROMYOGRAPHY

This is a continuation of copending application Ser. No. 07/558,638 filed on Jul. 27, 1990 now abandoned.

FIELD OF THE INVENTION

The present invention relates to a method and an apparatus for collection, analysis and presentation of myoelectric signals (EMG-signals) for determination of musclar status in accordance with the preamble of the independent claims.

BACKGROUND

In many contexts, there is a manifest interest in establishing muscular status, by which is taken to mean both the status of muscle at rest and the status of muscle at work. It is of particular interest to be able to follow the change in the status of the muscle during work and, in such instance, preferably to obtain a continuous and/or immediate information on status with the possibility of recording this for subsequent follow-up.

Such establishment of muscular status is, of course, interesting in purely scientific contexts and in the event of illnesses, but is also of considerable value in many practical applications, for example of people carrying out industrial assembly work or certain types of office work (e.g. terminal work at computers). By establishing muscular status, the possibility will be created, for example, for studying the effect of the design and layout of the workplace and the working position, respectively, on muscle loading, and for analyzing the consequences of prolonged monotonous muscle loading. This latter working situation occurs in both the assembly industry and in office work.

A correct establishment of muscular status in lengthy loading would make it possible, at best, to wholly avoid the risk of chronic muscular disorder or could be used to identify those stages of labor, which, for a given individual, cause, for instance chronic pain. The information would make it possible to modify the design of tools or the workplace in order to avoid such resulting or injuries. In particular, real time knowledge of the state of fatigue of the muscles could be essential in evaluating the effect of the work involved on the muscles.

It is obvious that there is also a need in this art for a technique for continuous recording of muscular status. Such a technique would, thus, make it possible to establish how muscular fatigue changes during a work shift or a series of work shifts, at the same time as such recording would make it possible to objectively analyze and identify how changes in the design of the workplace, for example the design of auxiliary aids, tools etc influence the degree of muscular fatigue and its development in prolonged work. It should be observed that, at low muscular loading which is continuous for a lengthy time, the individual himself does not observe that the muscle becomes fatigued. There are firm grounds for assuming that, when such situations exist, there is a risk of chronic muscular injury.

Also desirable is a technique which permits direct feedback to the individual of information concerning current muscular condition in order thereby to gain the possibility of warning, while work is in progress, of muscle loadings and stresses which risk resulting in injury.

SUMMARY OF THE INVENTION

The present invention seeks a method and apparatus which satisfy the above needs and wishes.

According to the present invention, use is made of the circumstances, that, the increasing muscular fatigue, the frequency spectrum of the EMG signal is shifted, the amplitude of the high frequencies decreasing and the amplitude of the low frequencies increasing. According to the invention, these circumstances are employed to generate an output signal which reflects the above indicated change of the frequency spectrum of the EMG signal.

The nature of the present invention and its aspects will be more readily understood from the following brief description of the accompanying drawings, and detailed discussion relating thereto, In the accompanying drawings:

DETAILED DESCRIPTION

Figure 1:
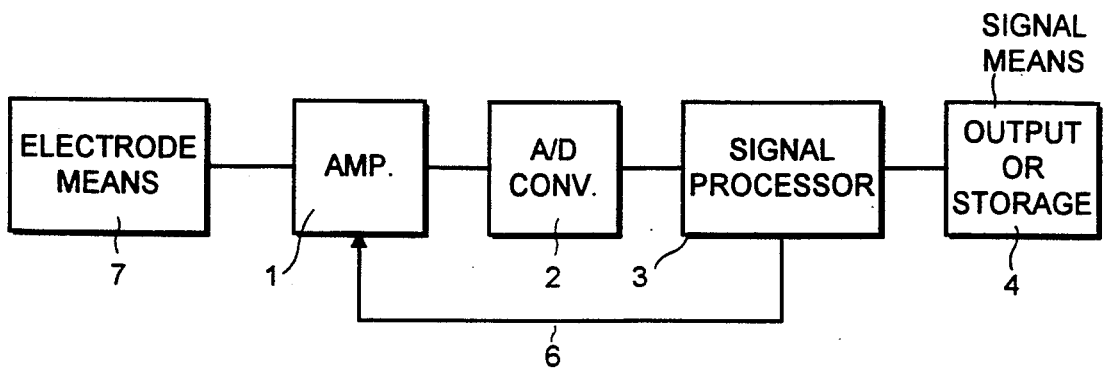
FIG. 1 is a block diagram of an apparatus according to the present invention.

An apparatus according to the present invention will now be described with reference to the block diagram in FIG. 1. This diagram shows an amplifier 1 to which is connected an electrode means 7 which is adapted to acquire analog myoelectrical signals (EMG-signals). The amplifier 1 is followed by an analog to digital converter (A/D-converter) 2 for converting analog signals emitted by the amplifier into digital (binary represented) signals. A signal processing unit 3 connected to the device 2 for analog/digital conversion (A/D-conversion) is operative for receiving digital signals emitted therefrom. In its turn, the signal processing unit 3 is coupled to or includes an output/storage device 4 for the output or storage of signals whose frequencies and/or amplitudes are related to the shift of the spectrum of frequencies within a given frequency interval of the analog electrical signals picked up by the electrode means 7. The stored signals are intended for subsequent output or analysis. Hereinafter, the term "signal means" 4 will be used to designate the output/storage device. When the signal means includes a unit for storage of information on frequency spectrum, the unit consists, for example, of a device for electric or magnetic storage of signals, for example a memory card, a tape memory, a diskette drive station, etc. In a preferred embodiment, a connection 6 connects signal processing unit 3 and the amplifier 1 for adjusting its amplification based on signals emitted by the unit 3. Requisite control and communication functions are included in the signal processing unit 3.

Figure 2:
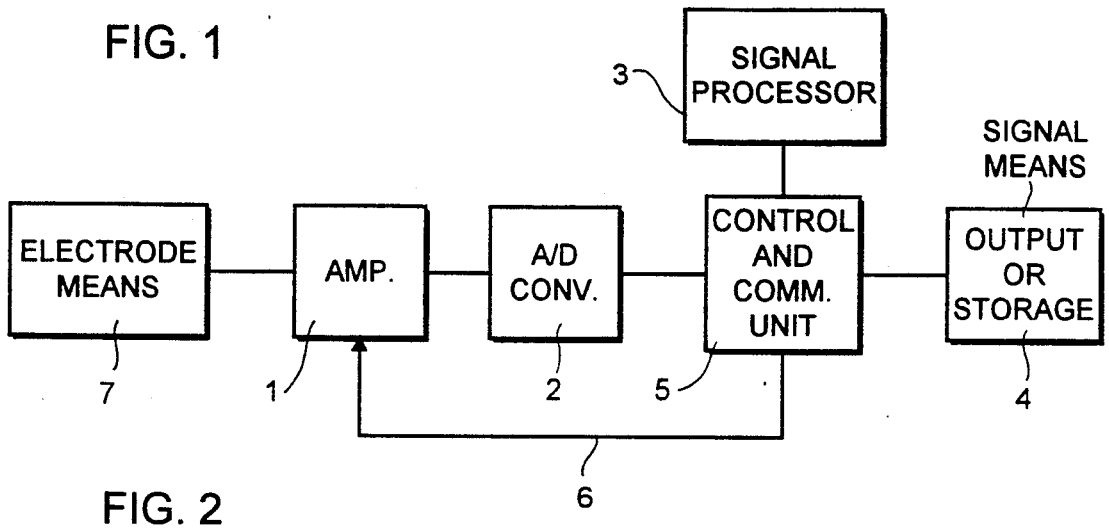
FIG. 2 is a block diagram of an alternative embodiment of the apparatus according to the present invention.

FIG. 2 shows an alternative embodiment of the apparatus in which a separate control and communication unit 5 is provided between the A/D converter 2 and the signal means 4. The signal processing unit 3 is connected to the control and communication unit 5. In the embodiments illustrated in FIGS. 1 and 2, the signal processing unit 3 and/or the control and communication unit 5 are, in certain cases, also arranged to include the signal means 4.

The electrode means 7 includes three electrodes which, in one preferred embodiment, are adapted to be applied to the skin of the person whose muscular status is to be examined. These electrodes detect the slight amounts of charge which are emitted by the muscles in the region of the body where the electrodes are attached.

The amplifier 1 includes the signal recording section of the apparatus. In the embodiment illustrated in FIGS. 3 and 4, the signal recording section includes a first amplifier stage 30 (cf. FIGS. 3) which, via a high pass filter 45 (cf. FIG. 4) is connected to a second amplifier stage 40.

Figure 3:
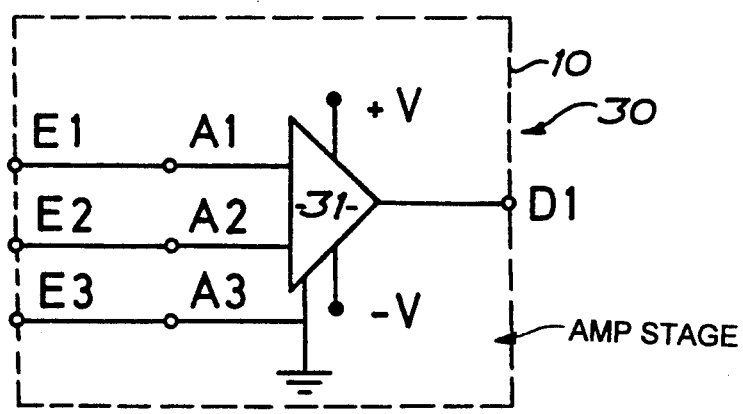
FIG. 3 shows an embodiment of a first amplifier stage included in the signal recording section of the apparatus.

According to the embodiment illustrated in FIG. 3, the first amplifier stage 30 includes a pre-amplifier 31 with three inputs A1, A2 and A3. In one preferred embodiment, the electrode means 7 includes three electrodes E1, E2 and E3 which are connected to the inputs A1, A2 and A3 of the pre-amplifier 31. In one preferred embodiment, the pre-amplifier 31 consists of an instrumentation amplifier. In the illustrated embodiment, the bipolar EMG-signal detected by the electrodes E1 and E2 is differentially amplified about 10 times. The third electrode E3 serves as a reference electrode. The voltage supply of the pre-amplifier is marked with the reference numerals $+V$ and $-V$, respectively, while its output has the reference numeral D1. The pre-amplifier 31 is so arranged that it has a high input impedance and a low noise. The high input impedance is required in view of the extremely low signal level of those signals which are sensed by the electrodes of the electrode means 7. The potential of these signals is of the order of magnitude of $10^{-7}$ to $10^{-3}$ V. The low noise factor is necessary so as to avoid the complication that the noise which is generated within the amplifier masks the weak signals which are sensed by the electrodes. By way of one example of a suitable amplifier, mention might be made of one manufactured by Johne & Reilhofer, designated EMGV1. A shield 10 is provided to protect the signal from electrical and/or magnetic disturbances. For high quality of the analysis of the signal, such shielding is of importance at least for those stages in the apparatus, in which the signal level has not yet been raised to a level at which the effect of such disturbances on the information content of the signal, is, as a rule, no longer of any importance.

Figure 4:
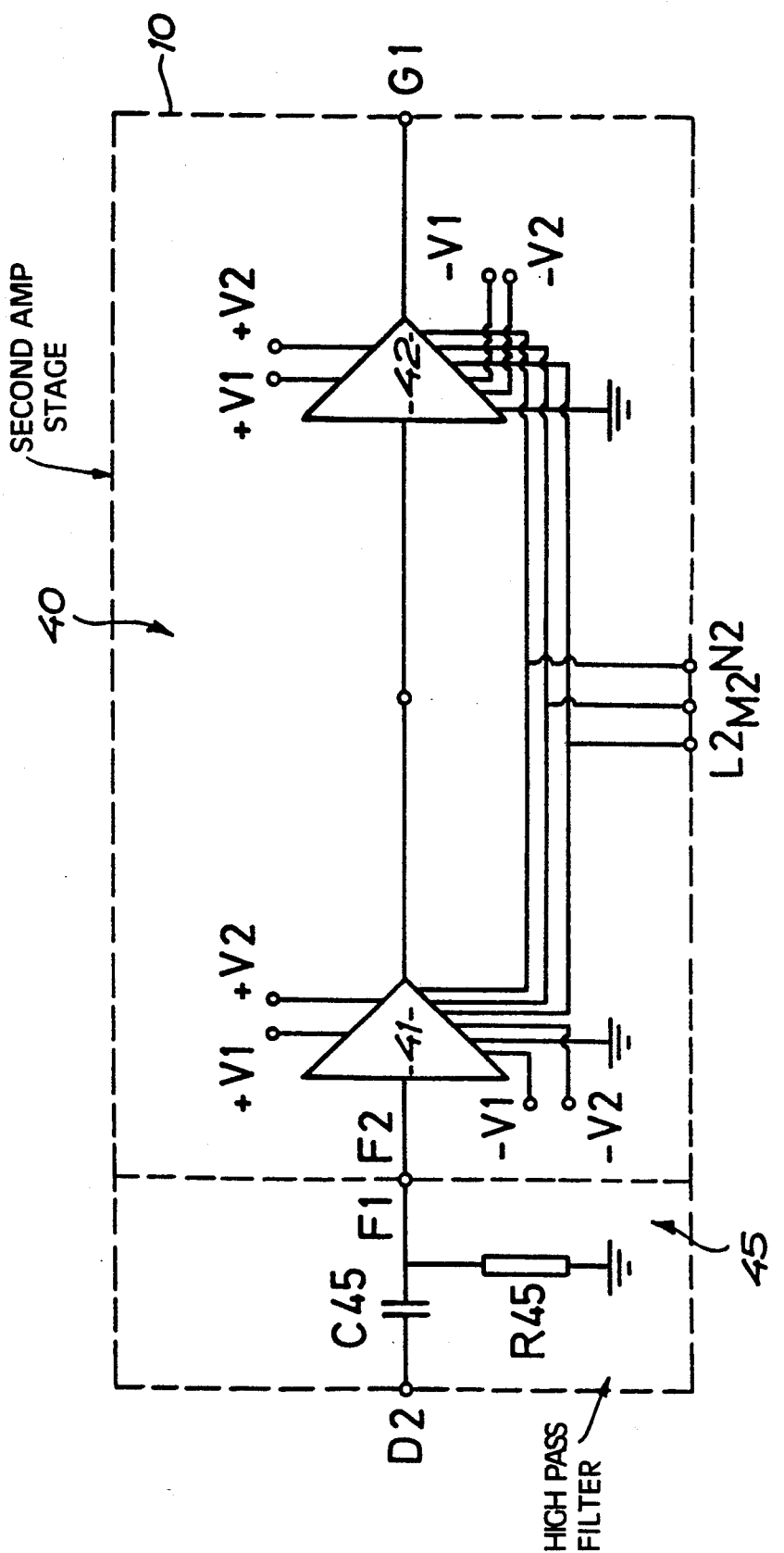
FIG. 4 shows an embodiment of a second amplifier stage included in the signal recording section of the apparatus.

FIG. 4 shows the high pass filter 45 designed as a passive RC-1 ink, C45, R45 with a lower limit frequency of at least approx. 1 Hz, as a rule at least 5 Hz, and preferably at least approx. 10 Hz. The input D2 of the RC link 45 is connected to the output D1 of the first amplifier stage 30, while the output F1 of the RC link is connected to the input F2 of the second amplifier stage 40, which in the illustrated embodiment, consists of two cascade-connected amplifiers 41, 42. In the illustrated embodiment, the cascade-connected amplifiers are of a design in which the amplification of each respective amplifier is set by means of binary signals and in which the cascade-connected amplifiers have, to this end, three binary inputs L2, M2, N2. In one preferred embodiment, the amplification is adjustable to 1, 2, 4, 8, 16, 32, 64 and 128 times. It will be obvious to one skilled in the art that the second amplifier stage, in other embodiments of the present invention, has a construction and amplification levels which may differ from those previously described. The voltage supply to the analog section of each respective amplifier is designated $+V1$ and $-V1$. The voltage supply to the digital section of each respective amplifier is designated $+V2$ and $-V2$.

Figure 5:
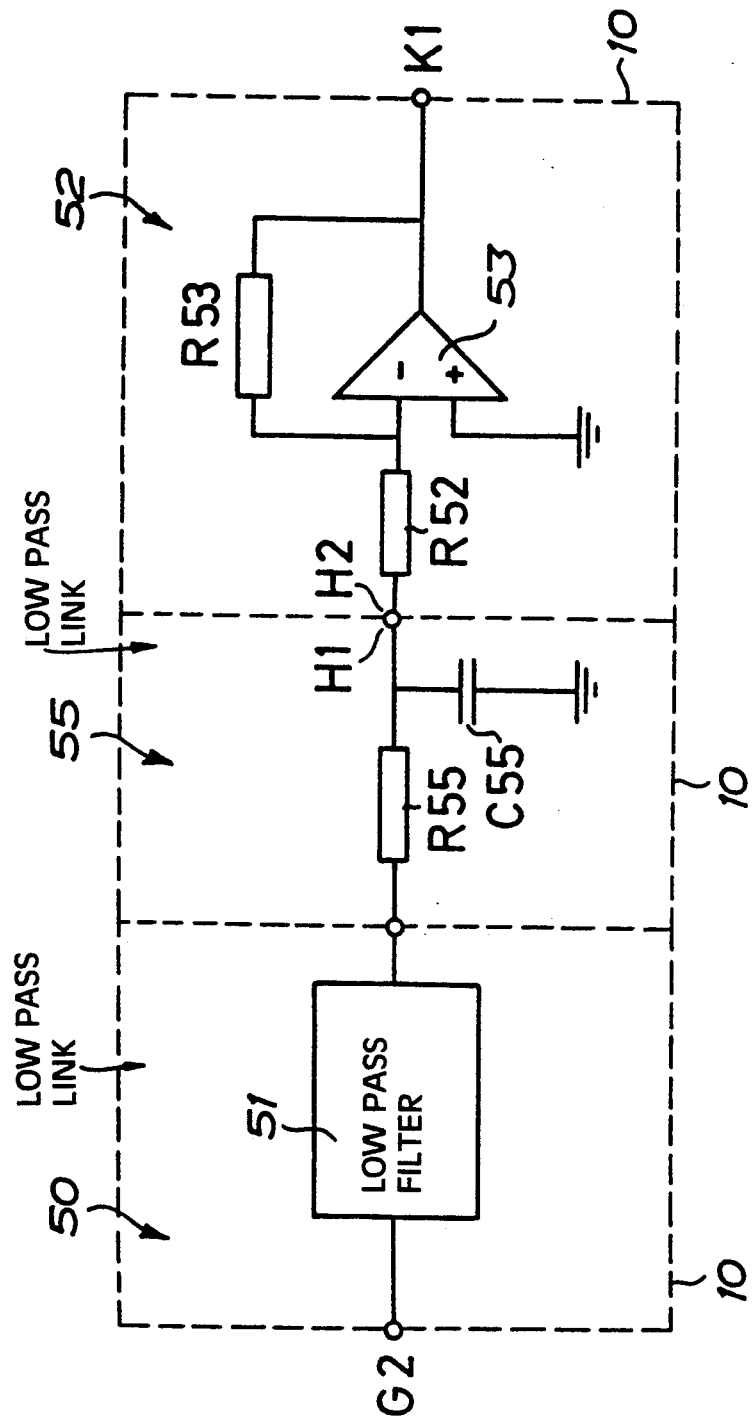
FIG. 5 shows one embodiment of a filter device followed by a third amplifier stage.

The output G1 from the cascade-connected amplifier stage 40 is, in one preferred embodiment, coupled to the input G2 of a first low pass link 50, ideally designed as an active low pass filter 51 (cf. FIG. 5). The requisite steepness of the filter will be achieved most simply by the employment of an active low pass filter. In one preferred embodiment, however a fifth order low pass filter of the Butterworth type is used. In such instance, filtering takes place in a "switched capacitor" filter. Hereby, the output signal will contain residues of a clock signal in which the residues are at a frequency which is 100 times the upper limit frequency of the filter. Consequently, the filter is followed by a second low pass link 55 in which the residues of the clock signal are removed. The figure shows an embodiment wherein a passive low pass filter is formed by a resistor R55 and a capacitor C55. In the described embodiment, the low pass link has an upper limit frequency of at most approx. 50 times, preferably at most approx. 25 times the limit frequency of the active low pass filter.

The output H1 from the second low pass link 55 is connected to the input H2 of a third amplifier stage 52, as a rule including an operational amplifier 53 whose amplification is adjusted by means of a resistor R52 connected between tile input H2 of the third amplifier stage and the negative input of the operational amplifier 53 and a second resistor R53 connected to the same input of the operational amplifier and to the output K1 of the operational amplifier.

In an embodiment of the present invention, use is made as active low pass filter 51 of a filter designated "Linear LTC1062", and as operational amplifier 53, the amplifier "Analog devices" AD548 or AD648. It will be obvious to one skilled in the art that, in other embodiments, an active low pass filter is selected which includes circuits for removal of all of the residues of the clock frequency which influence the subsequent analysis of the signal. Hereby, the second low pass link 55 may be omitted with from the apparatus. In a preferred embodiment of the invention, the total amplification of the signal from the input of the first amplifier stage 30 and to the output K1 of the third amplifier stage 52 is adjustable within the range of between 200 and 25600 times, The amplifier 1 described with particular reference to FIGS. 3-5 includes embodiments of the first amplifier stage 30, the high pass filter 45, the second amplifier stage 40, the first low pass link 50, the second low pass link 55 and the third amplifier stage 52 which correspond to a preferred design and construction of the amplifier 1. However, it will be obvious to one skilled in the art that, within the spirit and scope of the present invention, the separate sub stages which make up the amplifier may, in certain embodiments, be of deviating design and construction, that certain of the sub stages are wholly dispensed with or that certain sub steps are added without, for this reason, any major deviation taking place from the basic inventive concept as herein disclosed. Similarly, in certain embodiments, the sequence of the sub steps is modified, such that, for example the third amplifier stage 52 precedes the first low pass link 50.

Figure 6:
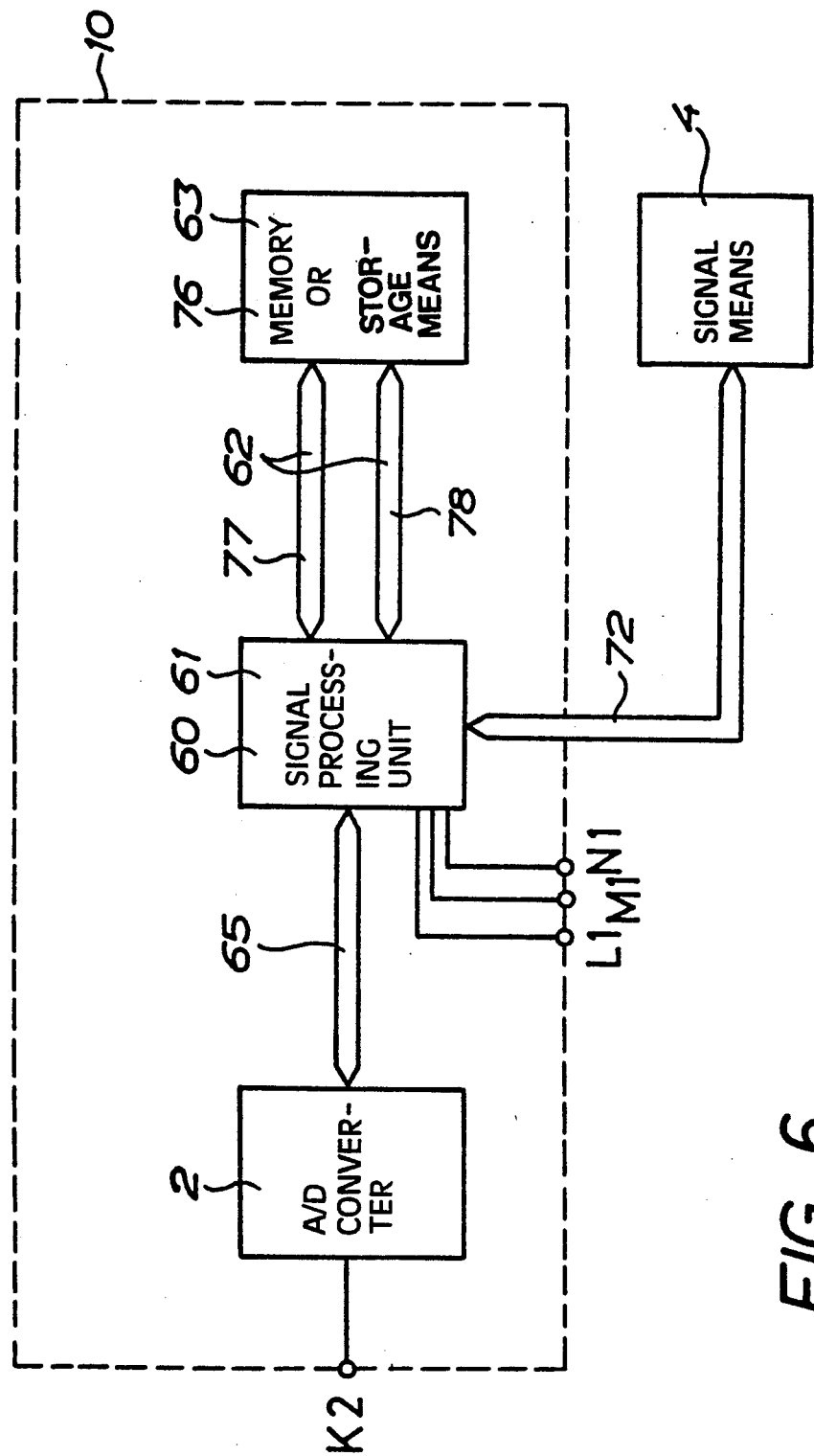
FIG. 6 shows a first embodiment of the apparatus for signal conversion, signal recording, signal analysis and display.

FIG. 6 shows the A/D converter 2 whose input K2 is connected to the output K1 of the third amplifier stage 52, In one preferred embodiment of the present invention, the A/D converter has at least 8, preferably at least 10 and as a rule at least 12 bits resolution. One example of a suitable A/D converter is "Crystal CS5012", The A/D converter 2 is, via a first signal connection 65, connected to a signal processing unit 60 which includes a signal processor 61 or microprocessor 61 of requisite calculation capacity. Hereinafter, the term signal processor will be used without restrictive significance. A memory 63 is connected to this processor by means of an address connection 77 and a data transfer connection 78. Hereinafter, the designation control connection will generally be employed for such a combination of connections, for which reason the previously disclosed combination of address connection 77 and data transfer connection 78 wi 11 hereinafter be designated first control connection 62. Between the signal processing unit 60 and the signal means 4, there is disposed a second control connection 72. The signal processing unit includes logic circuits for generating electric signals on the outputs L1, M1, N1 when the unit, for example the signal processor of the signal processing unit, identifies that the incoming signal to the unit represents signal values beyond predetermined limit values, for example excessively high or low effective values for frequencies included in the frequency spectrum. The outputs L1, M1, N1 of the signal processing unit are connected to the inputs L2, M2, N2 of the second amplifier stage 40 in order to form the feedback coupling 6 (cf. FIGS. 1 and 2) between the amplifier device 1 and the signal processing unit 3.

Figure 7:
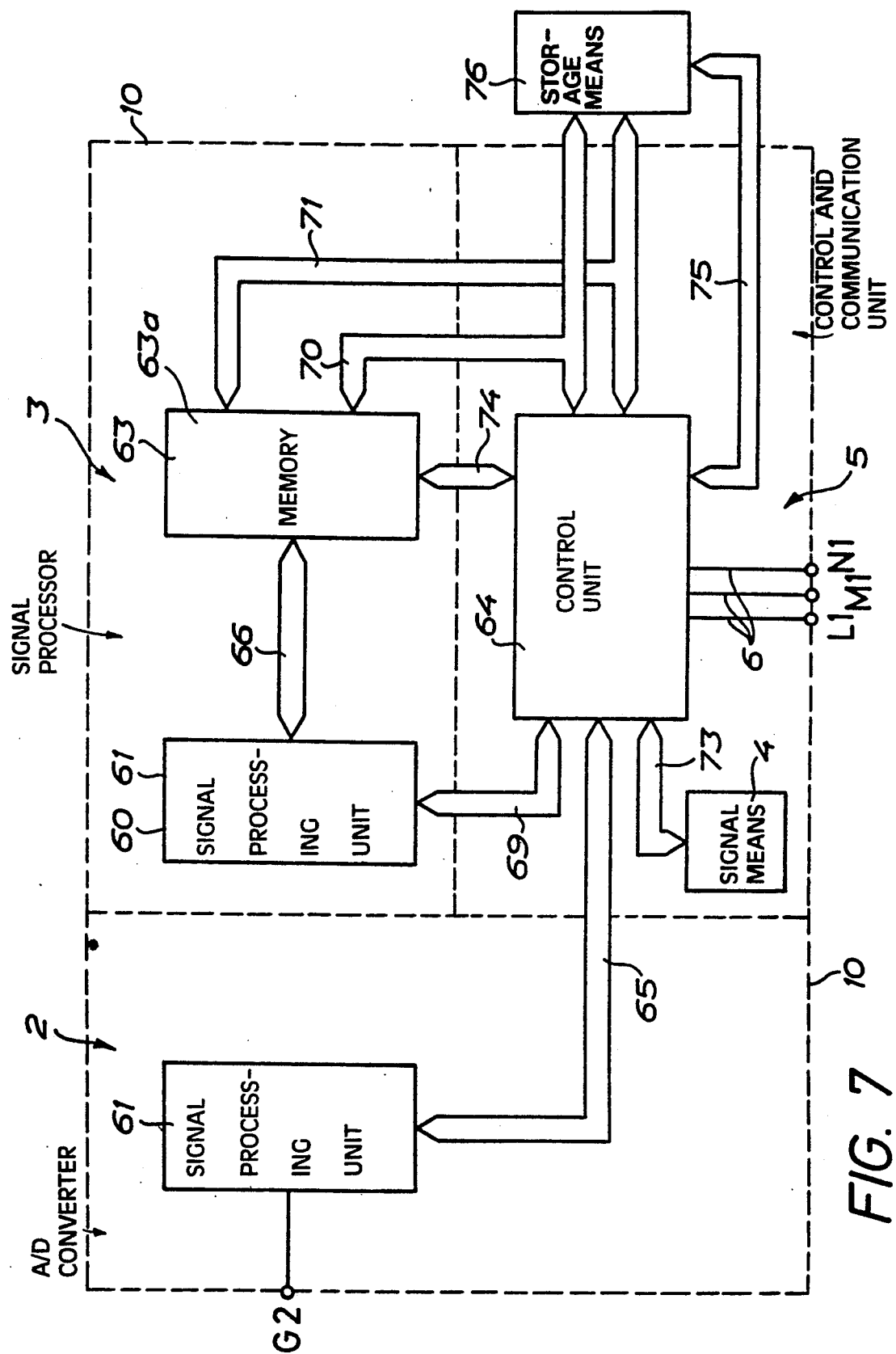
FIG. 7 shows a second embodiment of the apparatus for signal conversion, signal recording, signal analysis and presentation.

FIG. 7 illustrates an alternative embodiment of the present invention in which the A/D converter is connected to the control and communication unit 5, which, in its turn, is connected to the signal processing unit 60 and the memory 63. In the embodiment shown on the drawing, this consists of a dual-port memory 63a. Between the signal processing unit 60 and the dual-port memory, there is disposed a third control connection 66. The first signal connection 65 from the A/D converter, is, in this instance, connected to a control unit 64. A first databus 70 and a second databus 71 are connected thereto, with which both the dual-port memory 63a and the storage unit 76 are in communication. A fourth control connection 69 is disposed between the signal processing unit 60 and the control unit 64, a fifth control connection 74 is disposed between the control unit 64 and the dual-port memory 63a, and a sixth control connection 75 is disposed between the control unit 64 and a storage unit 76. A second signal connection or alternatively a seventh control connection 73, is disposed between the control unit 64 and the signal means 4. The control and communication unit 5, is in one preferred embodiment, also provided with outputs L1, M1 and N1 which are connected to inputs L2, M2 and N2 of the second amplifier stage 40 in order to form the feedback connection 6 between the signal processing unit 3 and the amplifier 1. The control unit 64 is shown as provided with the outputs. In certain embodiments, the storage unit 76 is included in the above-described signal means 4.

Figure 8:
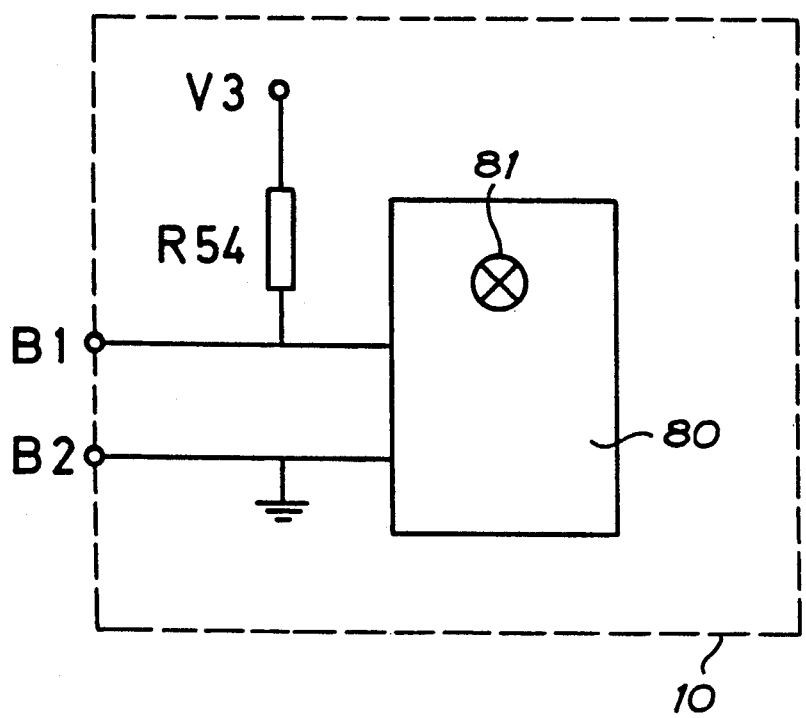
FIG. 8 shows an embodiment of a device for inspection of electrode contact.

FIG. 8 shows an embodiment of the present invention in which is included a unit for checking the quality of electrode contact between the electrode means 7 and the surface of the skin. A voltage source V3 is connected, via a resistor R54, to the one input B1 of means 80 with high input impedance, while the other input B2 of the means is grounded. The electrodes of the electrode means 7, with these applied on the surface of the skin, are connected pairwise to the two inputs of the unit and the impedance between the electrodes and the skin is determined by that voltage which said means 80 registers. An indicator 81, for example a signal lamp is used to indicate that too high voltage, and as a consequence too high impedance is present between electrodes and skin. The voltage source V3 is, in such instance, disposed via a resistor to be actuable and deactuable to one of the inputs of an amplifier e.g. the pre-amplifier 31 shown in FIG. 3. The voltage of the output of the amplifier is here employed as a measure of the impedance between the electrodes and controls the indicator. The measurement of the impedance provides the user with requisite information for improving electrode-skin contact on those occasions when the impedance is so high that measurement accuracy would have been jeopardized.

When the apparatus according to the present invention is reduced into practice the electrodes are applied against the skin in a region adjacent to that muscle whose status is to be established. Alternatively, at least one of the electrodes is inserted in the muscle. Every measurement occasion is unique and depends upon the specific conditions prevailing and upon such factors as skin thickness, attained skin-electrode contact, tissue attenuation etc. Consequently, it is necessary to begin each measurement with an adjustment of the amplification of the equipment and determination of the frequency spectrum of the specific muscle which is under examination. This adjustment process is a form of calibration of the equipment. In such instance, the patient assumes a position in which the muscle is subjected to a certain loading, whereafter the amplification of the amplifier 1 is adjusted such that the signal to the A/D converter assumes a value within a predetermined size range. Hereby, the size of the amplified signals will be adapted with reference to the size of the electric signals which are emitted from the muscle and the damping which occurs between the muscle and the electrodes.

The sensed signals are amplified and filtered in the amplifier 1, converted to binary signals in the A/D converter and passed to the signal processing unit 60. Herein, the frequency spectrum of the signals is analyzed and thereafter information on the configuration and/or location, e.g. median or mean value frequency of spectra are stored in the memory 63, 63a of the signal processing unit. The result of the analysis is continually stored and, in prolonged loading, a shift is, after a time, registered of the frequency spectrum towards lower frequencies in relation to the values registered during the "calibration".

Within the spirit and scope of the present invention, the signal processing unit 3 is, as a rule, programmed, so as on "calibration", itself to ascertain that a steady signal which represents the frequency spectrum and which has a signal level within a predetermined interval arrives at the signal processing unit. During the calibration and on a steady incoming signal, the signal processing unit is programmed to adjust, via the feedback connection 6, the amplification of the amplifier so that signal s transmitted to the signal processing unit are kept within the predetermined interval. On the "calibration" the configuration and location of the frequency spectrum are thereafter registered. The signal processing unit also attends to the modification of the amplification during the subsequent measurement process when the signal level is changed such that the levels of incoming signals to the signal processing unit are no longer located within the predetermined interval. The system is programmed, in the analysis of incoming frequency spectra, to compensate for adopted modifications of the amplification. In a preferred embodiment such compensation is made by the signal processing unit.

When the size of the shift exceeds a predetermined level, this is detected by the system e.g. by the signal processing unit 3 or by the control or communication unit 5 and a signal is emitted via the second control connection 72 or 73 to the signal means 4. It is evident to a person skilled in the art that the analysis of the frequency spectrum can be made by using any known method for analyzing and representing the frequency spectrum of a signal. As a rule, the signal means 4 is designed to receive binary signals which the signal means translates into, for example, acoustic signals whose amplitude and/or frequency for example increase as the frequency spectrum is shifted. In certain embodiments, the signal processing unit 3 emits a signal to the signal means 4 when the size of the shift of the frequency spectrum in relation to its original position exceeds a predetermined level during a predetermined minimum time interval, the signals emitted to the signal device being translated, for example, to acoustic signals whose intensity and/or frequency are modified when the shift of the spectrum of the EMG signal exceeds the predetemined level for a lengthy period of time. In certain embodiments the acoustic signals are replaced by optical signals, by tactile signals or by combinations of acoustic, optical and/or tactile signals.

As the rule, all signal processing steps in the apparatus are provided with a shield 10 which protects against electric and/or magnetic disturbances. At least shielding of those steps in the apparatus in which the signals are analog is of importance to protect these from superimposed disturbance or, in the worst case, wholly masking electric and/or magnetic disturbances. Such shielding is necessary in the establishment of muscular status for people carrying out working duties in environments where the external level of disturbance is high, for example certain working duties within the engineering industry, the automotive industry, etc.

The signal processing unit 3 is disposed as a rule by means of software, to establish the location and configuration of a frequency spectrum. The unit receives binary signals which it evaluates and classifies to generate at least one binary signal (parameter) which characterizes the frequency spectrum of the EMG signal. At each calculation said parameter or parameters are designated a value representing at least the location of the EMG signal in the frequency plane. In a preferred embodiment the parameter or parameters represent the shift of the EMG signal in relation to its original location. The expression "original location" means the location of the EMG spectrum on commencement of the detection.

The shift of the spectrum of frequencies is reflected by the signals emitted by the signal means 4.

The signal processing of the EMG signal is executed in data sequences comprising a certain number of samples and a correspondingly adapted sample frequency. In one preferred embodiment, the combination of a sampling frequency of 1024 Hz and data sequences of 256 samples has been employed. This choice also determines the upper limit frequency of the active low pass filter 51 to a practical level of approx. 400 Hz (the sampling theorem gives the theoretical value of 512 Hz). It is obvious that, on certain measurement conditions, the limit frequency may need to be selected to be lower. A halfing of the limit frequency is, as a rule, more than sufficient. Alternatively, the option may be chosen, in such situations, to increase the sampling frequencies. The location and configuration of the frequency spectrum are determined by means of a Fourier algorithm which divides the original signal into different frequency bands. The resolution in the frequency plane is determined by the ratio of the sampling frequency and the data sequence length. By using computerized signal processing, the systems sensitivity to disturbances is reduced, frequency analysis is facilitated and possibilities are opened for combining continuously provided information on muscular status with registration of muscular status (spectrum of frequencies) during a lengthy period of time, for example for subsequent analysis.

In greater detail, it applies on using the design and construction of the amplifier 1 as illustrated in FIGS. 3–5 that the signals from the electrodes E1, E2 of the electrode means 7 are fed to the inputs A1, A2 of the pre-amplifier 31 of the first amplifier stage 30. The differential input of the pre-amplifier reduces disturbances deriving from the mains frequency and disturbances of types such as motion artefacts. The output signal from the amplifier stage passes via its output D1 to the input D2 of the high pass filter 45, in which the D.C. voltage component of the signal is filtered off and present low frequency disturbances such as motion artefacts are further damped. The thus processed signal continues via the output F1 of the high pass filter to the input F2 of the second amplifier stage 40 and, after amplification therein, via its output G1 to the input G2 of the first low pass link 50 in which substantially all frequency components above a predetermined upper limit frequency and included in the signal emitted by the second amplifier stage 40 are filtered off. The signal is thereafter fed to the second low pass link 55 in which any possible residual undesired frequency components are removed. For example when use is made of an active low pass filter in the first low pass link 50, traces of a clock signal employed in the low pass filter are, where applicable, removed. The thus processed signal is fed, via the output H1 of the second low pass link to the input H2 of the third amplifier stage 52. From the output K1 of the third amplifier stage, the signal is thereafter fed to the input K2 of the A/D converter 2. The signal is now limited to the frequency range within which EMG signals of interest occur and are amplified to a level which makes it suitable for transfer to the A/D converter.

According to the embodiment illustrated in FIG. 6, the signal emitted in binary form from the A/D converter is transmitted via the first signal connection 65 directly to the signal processing unit 60. Therein, the above described analysis of the signal takes place, in which event the signal processing unit, via the first control connection 62 stores information in the memory 63, the memory constituting, on the one hand, an intermediate store medium during analysis by the signal processing unit of the incoming signal, and, on the other hand, generally constitutes a temporary memory for storage of the result of the analysis by the signal processing unit. In certain embodiments, the memory 63 is upgraded so as also to constitute a storage unit 76 for permanent storage of information represented in binary form. In certain embodiments, the storage unit corresponds, in this instance, to the signal means 4.

Once the signal processing unit has completed the analysis of the incoming signal, the result of such analysis is passed via the signal connection 72 to the signal means 4 and/or to the permanent storage unit 76. The signal processing unit 60 or in some embodiments the control unit 64 constitutes that device which, via the first signal connection 65, controls the A/D converter for the sampling of the data sequences as described above. During ongoing analysis of a data sequence, the signal processor 61 allows incoming signals from the A/D converter to pass to the memory 63 to be stored therein and fed back to the signal processor in conjunction with its analysis of the data sequence which follows upon the data sequence which the signal processor is currently engaged in analysing. Signals on the outputs L1, M1, N1 are fed back to the inputs L2, M2, N2 of the second amplifier stage 40 for adjustment of the amplification.

In the embodiment illustrated in FIG. 7 the A/D converter 61 emits its binary signals via the first signal connection 65 to the control unit 64. In such instance, the control unit 64 controls the A/D converter for sampling of the data signals. The signal is further transmitted from the control unit via the first data bus 70 to the dual-port memory 63a. The control unit simultaneously controls addressing of the information storage via the fifth control connection 74. When the control unit registers that a complete data sequence has been stored in the memory 63a, the control unit controls, via the fourth control connection 69 the signal processor 61 so that this retrieves information via the third control connection 66 concerning the recently stored data sequence in the memory 63a for analysis of its frequency contents. When the analysis has been completed, the result thereof is transferred to the dual-port memory, at the same time as the control unit 64, via the fifth control connection 74, ensures that information corresponding to the analysis result stored in the memory 63a is retrieved from the memory via the second data bus 71. Here, the control unit guides the information to the storage unit 76, to the signal means 4 or to both the storage unit and the signal means.

In certain embodiments, the signal means 4 constitutes a part of the signal processing unit 3. As a rule, the storage unit 76 is connected in so as to make possible easy replacement of storage units and to make possible the retrieval of information from every separate storage unit on a later occasion, for example to a computer hardware and thereafter processed therein. The disclosures of this paragraph apply to both the embodiment according to FIG. 6 and the embodiment according to FIG. 7.

It is obvious that the technique described above provides the possibility for extremely compact design and construction and immediate information on the results of the analysis of the extracted EMG signals. In certain embodiments of the present invention, the equipment is designed to be portable, whereby it may be used direct at the workplace during daily work without constituting any appreciable hindrance to the user. The above immediate indication of muscular status for example makes it possible to rapidly implement measures to avoid injury arising out of an unsuitably designed schedule or program of movement. It also provides the possibility of practicing suitable techniques for movement in preventive or rehabilitation purposes and also the possibility for evaluating those ergonomic measures which should be implemented to improve the working environment. It is also obvious that the possibility encompassed by the present invention for continuous recording during a lengthy period of time for muscular status for an individual muscle group opens up opportunities for results follow-up of the muscular status of individual people, for example for research purposes.

The present invention is also of value given the fact that load strain illnesses, have, in recent years, shown a marked tendency to increase probably because more and more static and repetitive loading moments have become included in working life.

Studies in working life in respect of measurement, analysis and remedial proposals have earlier been difficult to carry out since there has been no simple and dependable measurement equipment for routine load studies. However, the present invention makes such studies possible.

In this context, it should be observed that it is difficult to carry out muscular load studies since there are no adequate mechanical models for loading conditions in muscles. The present invention makes it possible, in connection with muscular activity, to sample and analyze the signals transmitted by the muscles either directly within the muscle itself or, for superficial muscles, by electrodes applied to the surface of the skin.

According to the present invention muscle status is indicated by the shift of the frequency spectrum. As a consequence an essential advantage is obtained as variations in the level of the acquired myoelectric signal could be compensated by an adjustment of the amplification of the signal, which in turn means that the signal level always has a value ensuring an analysis without any substantial impact from disturbances and noise. By checking the configuration (shape) of the frequency spectrum, amplification could be excluded when the signal only consists of noise.

The invention also makes it possible to eliminate frequencies around the power frequency, which means that the detection of the muscle status could be made without any impact of non relevant information emanating from disturbancies caused by the power supply.

The above detailed description has referred to but a limited number of embodiments of the present invention, but one skilled in the art will readily perceive that the present invention encompasses a large number of embodiments without departing from the spirit and scope of the appended claims.

What is claimed is:

1. A method for detecting substantially continually, over a period of time, muscular status to determine muscular fatigue, said method comprising producing analog myoelectric signals in response to activity of a muscle under examination, amplifying said signals to produce amplified signals, converting the amplified signals into digital signals, in successive calculation periods, producing from said digital signals a signal which characterizes a frequency spectrum of each of said myoelectric signals during each calculation period, comparing the signals which characterize the frequency spectrums to a base signal representing the frequency spectrum on commencement of said period of time of detection, producing output signals based on said comparing to represent muscular status for detecting muscle fatigue based on shift of said frequency spectrums beyond a predetermined value, and transforming said output signals representing muscular status into a state perceivable by a human being.

2. The method of detecting muscular status as claimed in claim 1, comprising storing in a signal processing unit the digital signals relating to the frequency spectrum of the myoelectric signals and the frequency shift thereof.

3. The method of detecting muscular status as claimed in claim 1, comprising producing a signal when any shift of the frequency spectrum exceeds said predetermined value thereby to signal muscular fatigue.

4. The method of detecting muscular status as claimed in claim 1, wherein said output signals are transformed into the state perceivable to a human being at least one of an optical, acoustical and tactile signal.

5. The method of detecting muscular status as claimed in claim 4 comprising forming said output signals with one of amplitude and frequency related to a shift of the frequency spectrum.

6. An apparatus for substantially continually detecting muscular status to determine muscular fatigue comprising electrode means for producing analog myoelectric signals related to muscular activity of a muscle of a subject under examination, amplifier means for amplifying said signals, A/D converter means connected to said amplifier means for converting said analog signals into digital signals, signal processing means connected to said A/D converter means for receiving signals therefrom and forming intermediate signals related to the frequency spectrum of the myoelectric signals at periodic intervals, said signal processing means including means for detecting, at said periodic intervals, shift in the frequency of the frequency spectrum of said intermediate signals in relation to an initial frequency, in a calibration period when first receiving the myoelectric signals, means for emitting, during each said interval, at least one signal representing muscular status of the muscle under examination based on said shift of said frequency spectrum in relation to said initial frequency and for producing an output to indicate muscle fatigue if said shift of said frequency spectrum exceeds a predetermined value, storing means for storage of the signals representing the shift of the frequency spectrum, signal means for transforming said signals representing muscular status into information which is perceivable by a human being, and means for connecting at least one of said storing means and said signal means to said signal processing means.

7. The apparatus as claimed in claim 6 wherein said information from said signal means comprises a signal which is at least one of optical, acoustic, and tactile signals.

8. The apparatus as claimed in claim 6 wherein said signal means produces signals having a characteristic related to the shift of the frequency spectrum within a predetermined frequency range for the signals produced by the electrode means.

9. The apparatus as claimed in claim 8 wherein the characteristic of the signals produced by the signal means is at least one of amplitude and frequency.

10. The apparatus as claimed in claim 6 wherein said signal means includes means for converting electrical signals to acoustical signals.

11. The apparatus as claimed in claim 6 comprising control and communication means interconnected between said signal processing means and said signal means.

12. The apparatus as claimed in claim 11 wherein said control and communication means emits signals which are at least one of analog and digital.

13. The apparatus as claimed in claim 11 wherein said control and communication means supplies control signals to said signal means for adjusting at least one of the frequency and amplitude of the signals produced by said signal means.

14. The apparatus as claimed in claim 6 comprising control and communication means connected to said signal processing means and including said signal means.

15. The apparatus as claimed in claim 6 wherein said signal means produces signals having amplitude and frequency, at least one of which is changed when the frequency spectrum of the signals produced by the electrode means is shifted towards lower frequencies.

16. The apparatus as claimed in claim 6 wherein said signal processing means supplies control signals to said signal means for adjusting at least one of the frequency and amplitude of the signals produced by said signal means.

17. The apparatus as claimed in claim 6 wherein said storing means stores digital information relating to the frequency spectrum of the myoelectric signals produced by the electrode means, said storing means being separable from the apparatus.

18. The apparatus as claimed in claim 6, comprising means for establishing a threshold for said predetermined value of the shift of frequency spectrum from the frequency measured during the calibration period, said means for emitting, during each said interval, at least one signal representing shift of said frequency spectrum including means to send a signal to said signal means to produce an alarm signal when said threshold is exceeded.

* * * * *